United States Patent [19]
Goldman et al.

[11] Patent Number: 5,542,420
[45] Date of Patent: Aug. 6, 1996

[54] PERSONALIZED METHOD AND SYSTEM FOR STORAGE, COMMUNICATION, ANALYSIS, AND PROCESSING OF HEALTH-RELATED DATA

[76] Inventors: Arnold J. Goldman, 55 Bar Kochbar St., Jerusalem 97890; David L. Greenberg, 13 Even Shmuel St., Jerusalem 91230, both of Israel

[21] Appl. No.: 237,012

[22] Filed: Apr. 29, 1994

[30] Foreign Application Priority Data

Apr. 30, 1993 [IL] Israel ........................................ 105563

[51] Int. Cl.⁶ ............................. G06F 15/00; A61B 5/00
[52] U.S. Cl. ..................................... 128/630; 364/413.29
[58] Field of Search .................................. 128/630, 897, 128/898, 904; 364/413.01, 413.29, 413.02, 413.03

[56] References Cited

U.S. PATENT DOCUMENTS

| | | |
|---|---|---|
| 4,731,726 | 3/1988 | Allen . |
| 4,924,389 | 5/1990 | Gerbaulet et al. ................ 364/413.29 |
| 4,954,954 | 9/1990 | Madsen et al. .................... 364/413.29 |
| 5,233,520 | 8/1993 | Kretsch et al. .................... 364/413.29 |
| 5,301,105 | 4/1994 | Cummings, Jr. . |

FOREIGN PATENT DOCUMENTS

| | | |
|---|---|---|
| 0290683 | 11/1988 | European Pat. Off. . |
| 0462466 | 12/1991 | European Pat. Off. . |
| 0222136 | 12/1984 | Japan . |
| WO93/07570 | 4/1993 | WIPO . |

OTHER PUBLICATIONS

Gomez E., et al., "The Use of the Diacrono as an Aid in Ambulatory Decision Making of Diabetic Patients," *Proceedings of the Twelfth Annual International Conference of the IEEE Engineering in Medicine and Biology Society*, Nov. 1–4, 1990, vol. 12, No. 3 (Part 3/5), pp. 1226–1227 (XP 000244746).

Gomez–Aquilera, E.J., et al., "Diacrono: A New Portable Microcomputer System for Diabetes Management," *Proceedings of the Ninth Annual Conference of the IEEE Engineering in Medicine and Biology Society*, Nov. 13–16, 1987, vol. 3 of 4, pp. 1231–1232 (XP 000040726).

Saudek, C.D., "Data Source Automation: New Technology for the Management of Patient Generated Test Results", *Diabetic Medicine, Journal of the British Diabetic Association*, Jul. 1989, vol. 6, No. 5, pp. 394–399.

*Primary Examiner*—Angela D. Sykes
*Assistant Examiner*—Samuel Gilbert
*Attorney, Agent, or Firm*—Darby & Darby P.C.

[57] ABSTRACT

The present invention relates to a health care system for specifying edibles to individual subjects. The personalized method and system for storage, communication, analysis and processing of health-related data comprises a storage containing data relating to health and edibles and is adapted to receive data on the conditions and characteristics of the individual subjects. The health care system further comprises input terminals adapted to be coupled to the storage means for providing data on the conditions and characteristics of the individual subjects, and a health computer for correlating the data relating to health and edibles with the data on the condition and characteristics of an individual subject to provide a personalized prescription of edibles.

10 Claims, 9 Drawing Sheets

PERSONALIZED METHOD AND SYSTEM FOR STORAGE, COMMUNICATION, ANALYSIS, AND PROCESSING OF HEALTH–RELATED DATA

FIELD OF THE INVENTION

The present invention relates generally to a method and system for providing a comprehensive, yet cost effective, approach to the general health and well being of individuals. More particularly, the present invention relates to a method and system for storage, communication, analysis and processing of health data relating to individuals, accessible to all approved subscribing entities, such as healthcare providers including doctors, hospitals, wellness centers and the like, pharmacies, individuals and so on. The method and system of the present invention may be used for diverse health-related applications, as for example, in a nutritional application for prescribing edibles for persons on an individual basis to approximate actual needs for health and well being. In another exemplary pharmaceutical application, the method and system of the present invention may be used for enabling cooperation and communications between doctors and pharmacies, as for prescribing and dispensing medications. Similarly, in geriatric, as well as other applications it may be used for administering and monitoring organized drug and/or food regimens and may be used for more effectively prescribing medication greatly reducing side effects because it will be possible from established individually oriented data bases to learn to correlate specific side effects with specific personal characteristics and thereby prescribe medication minimizing these side effects. It may be used to guide an individual in a food store (electronic or physical) to pick the most health beneficial food brand of a particular food type based on current personal health characteristics and current state of nutritional knowledge. It may be used to help particular producers of health products locate the very specific potential users who would benefit most from their products and so on.

BACKGROUND AND SUMMARY OF THE INVENTION

Over the years, despite rapid advances in computer technology involving improved data accumulation, transfer and processing techniques, the health-related fields have continued to utilize dated and expensive techniques. For example, at present healthcare providers are generally only able to offer isolated and specialized care, targeting an individual's specific maladies, rather than, offering a comprehensive approach to the individual's health and general well being. The data required to provide enhanced care is not easily accessible to healthcare providers, without the expenditure of extraordinary efforts and funds.

By way of a nutrition-related example, a vast amount of data exists on the relationship between personal health and edible consumption. The United States National Institute of Health routinely evaluates such data and lists specific recommended daily allowances (RDA's) of various edibles. For example, various important nutritional substances, such as minerals, vitamins, antioxidants, as well as various pharmaceuticals, such as aspirin, diuretics, anti-inflammatory drugs are specified in various quantities to address the needs and tolerances of people in general. However, for the most part, such data is generic, treating human beings in general and not particular human beings. With all their specific differences individualized treatment for persons has not been effectively utilized on a wide scale basis. Thus, a need continues to exist for obtaining and utilizing meaningful data, particularly on an individual basis.

At the outset, some definitions will be helpful in disclosing exemplary applications of the present invention. The term "edible" encompasses substances taken orally, including various nutritives and food substances, such as vitamins, minerals and so on, as well as pharmaceutical substances, such as various drugs used for the treatment of chronic, as well as acute clinical conditions. A specification of edibles to approximate the actual needs of an individual will be referred to herein as a "personalized prescription." The term "personalized" implies that the quantities of ingredients serve an individual's needs, independent of generalized or standardized doses as typically contained in off-the-shelf medications or food preparations. The term "health profile" specifies the character, health, needs, habits, and so on of an individual subject. Basically, profiles are established for subjects as a basis for generating "personalized prescriptions".

Generally, the present invention involves a system, encompassing a structure and a process, for accumulating, storing, analyzing and processing health-related data for individuals (profiles) along with edible data, as basis for specifying personalized prescriptions. The system utilizes a form of apparatus effective for the collection of health-related information and data, and for the processing of such information and data monitoring the application of processing results.

One of the most problematic areas in nutritional analysis is the collection of comprehensive dietary intake information for effective use by a dietician, analyst, or the like, i.e., for developing an accurate record of what a subject typically consumes. Traditionally, a subject is requested to keep a record of all foods eaten during a three day period. Usually, motivation tends to wane after three days. The record may be written in a tabular form, listing specific foods, quantities and so on. However, regardless of the format, the activity tends to be burdensome, tedious, and somewhat ineffective.

To consider an example, assume a subject has consumed a simple breakfast consisting of one slice of bread with margarine, a glass of milk and an apple. To record the meal in such terms is easy, but nutritional analysis of the meal is next to impossible. For example, a nutritional program may include as many as 160 listings under bread. Thus, "bread" by itself is of little help to the dietician. Prior techniques have suggested some selectivity, such as "wheat bread." However, even crude selectivity is time consuming and subjects have little tolerance for it. Similar problems exist with respect to apples, margarine and many other consumables. Thus, usually, the data is somewhat questionable.

In addition to the basic problem of data acquisition and recording, initial processing also poses a problem. In that regard, it is practically impossible for an individual to communicate detailed personal circumstances to a listening health professional and obtain optimum personal advice. Even if such arrangements were possible, the procedure would be incredibly expensive. Typically, professional health practitioners are overwhelmed. They face the need of seeing a set number of patients every hour, while keeping up with new findings in their field. Consequently, the problem of questionable data is compounded by ineffective communication and processing.

As a further complication of health administration, pharmacies are constrained to drug products with standard doses and compelled to concentrate on order forms and insurance company procedures. To a large extent, they are unable to effectively integrate either the patient/customer or the products with a knowledge base. Rather, they are deterred in the role of a medically-intelligent dispatching/delivery system.

Drug prescriptions are rarely based on any attempt to delve into individual human differences with knowledge of a product, together with the individual's genetic, psychic and cultural background, family history and nutrient consumption. Patient records are often inadequate or ignored in the prescription of drugs. Personal health issues are pushed aside on the basis of statistical processing, standard doses, and shallow relationships. Accordingly, a substantial need exists for an improved system (method and apparatus) for implementing a person's consumption of edibles to approximate the person's actual health needs.

In a related context, in typical situations, a doctor provides a prescription to an individual, who in turn presents it to a pharmacy to be filled. The prescription administered by the doctor seldom takes into account the effect of the drugs prescribed or any extreme characteristics that the individual may have, generally because the individual's accumulated history is not necessarily available to either the doctor or the pharmacy. Moreover, typically there is no direct communication between the doctor and the pharmacy, whereby prescriptions can be fine tuned or the pharmacy may provide the doctor with the results of drug interaction analysis.

In general, the system of the present invention integrates the technological capabilities of current communication and data processing techniques with accumulation and storage of medical and health-related knowledge relating to individuals. Using various apparatus, including telephonic terminals, such knowledge may be accumulated over time, from multiple and varied sources, such as doctors, hospitals, medical laboratories, pharmacies, dieticians, as well as individual patients themselves.

Heath-related data for individuals to be serviced by the system may be continually and automatically updated by all subscribing entities. In addition, data on unknown individuals may also be accumulated for future use as data on individuals not actually in the program. The system provides access to approved entities, enabling direct communication between remote parties, as well as providing an accurate and comprehensive database of knowledge to ensure personalized care.

In one application, the system may define and deliver edibles approximating an individual's actual needs. For example, the system of the present invention may provide a subject with prescription drugs designed to approximate an individual's needs exactly, with a diet similarly designed for the same person, or with a combination of the two.

A personal prescription in accordance herewith may improve the health and welfare of healthy individuals, as well as persons suffering from various diseases or disorders. The invention is based on the recognition that rather than prescribing "average" or "standard" products, e.g., products designed for the average individual, more precise personal needs can be defined. Such needs should take into consideration demographic characteristics, eating habits, personal health, health history, family history, work, physical activity and so on.

Somewhat more specifically, the system of the present invention involves prescribing edibles to individuals based on:

(a) obtaining a first set of data including physical and health information and other personal parameters, which determine the individual's requirements for edibles; such parameters might include sex, age, weight, type of work performed, working hours, sport activities, smoking habits, daily drug intake, and so on;

(b) determining an individual's requirements for edibles including pharmaceuticals, minerals, vitamins, antioxidants, fats, proteins, carbohydrates and so on;

(c) obtaining a second set of data on the individual's average daily food and drug intake over a meaningful interval;

(d) comparing and correlating the data to determine an individual's deficiencies of edibles; and (e) prescribing for the individual with one or more drugs, combinations of drugs, food products or other combinations with the objective of supplying needs and compensating deficiencies.

To implement the system of the present invention, various technologies are combined. Specifically, communication facilities (e.g. telephone) are utilized in cooperation with data input devices, computers and processors to store, analyze, communicate and process data, such as to determine an individual's recommended intake quantities (RIQ), formulate. and package prescriptions and monitor, as well as to modify and refine the person's intake. Techniques are incorporated for effectively collecting, processing and utilizing data to accomplish personalized prescriptions. Additionally, the system enables a drug-preparation pharmacy for the implementation of personalized prescriptions in the form of edibles or the like for substantially meeting the specific requirements of individuals. The pharmacy may combine numerous elements or select edibles for packaging in a few capsules for a specific individual. In addition, the personalized prescription pharmacy also may provide the individual with custom food preparations and prescriptions as in a hospital or treatment environment.

Alternatively, the pharmacy may assemble individual regimens which dispense pills of specific dosages and at specific frequency which allow a person's individual needs to be met over a time averaging period like one week or in some cases one month depending on the specific substance and the bodies natural capacity for storing and releasing the substance.

Considering the structural aspects of the system of the present invention in somewhat greater detail, a portable terminal as in the form of a personal computer or automated notebook may be provided to a subject for recording preliminary information, as well as food intake. Additionally, an attached portable bar-code reader may be provided for easy recording of data. Where food manufacturers or restaurants have bar-codes, which are on the package or menu, and specify food data like bistro, macro and micro nutrients per unit of food consumed, data entry is facilitated. In a telephonic communication, the operation may be refined as with audio cues or prompts. In response to entering the consumption of a slice of bread, the subject could be prompted so as to attain greater specificity, for example, "white or dark?"; "whole wheat or not?" and so on.

Typically, a central system (data bank and processor) will interface the subject terminals and also includes capability for communicating with other remote terminals at doctors' offices, hospitals, wellness centers or the like, pharmacy terminals, billing terminals and formulation terminals. Periodically, information entered in a terminal by an individual, doctor or laboratory technician is collected or downloaded to the central station system, online as by utilizing telephone communication, or in some cases, off-line as by facsimile or the like if the need arises.

At the central station, processing and storage facilities are provided to generate and refine the needs of the subject and to provide a personalized prescription or guidance data to the individual, as well as to provide health-related data to any of the accessing entities. The central station incorporates communication interface facilities, a substantial data base of health-related data, such as nutritional information and logic for analyzing and correlating input data, ultimately to define a subject's profile and personalized prescription, further to detect critical conditions or enable healthcare providers to provide better care. Operators or analysts utilizing terminals of the central station may enter person-to-person communications if a need is sensed by a subject or sensed by the system logic.

The individual file can be processed by preventative health information which might from time to time become available and might be used for early detection of disease where early action may be helpful. Regimens are dispensed in dosages at certain levels and modulated by frequency of dosages when total intake requirements are met or exceeded. The database can be utilized for scanning against a universe of available products which are available in the database and may be particularly useful for optimizing a person's dietary and pharmaceutical needs. The universe of product files can be used to scan against subject files to find the individuals who could most effectively use their products.

BRIEF DESCRIPTION OF THE DRAWINGS

In the drawings, which constitute a part of the specification, exemplary embodiments exhibiting various objectives and features hereof are set forth, specifically.

DESCRIPTION OF THE ILLUSTRATIVE EMBODIMENT

As required, a detailed illustrative embodiment of the present invention is disclosed herein. However, specific communication systems, data and storage formats, health data processing structures health and dietary formats, and so on may be embodied in a wide variety of forms, some of which may be quite different from those of the disclosed embodiment. Consequently, the specific structural and functional details disclosed herein are merely representative; yet in that regard, they are deemed to afford the best embodiment for purposes of disclosure and to provide a basis for the claims herein which define the scope of the present invention.

Figure 1:
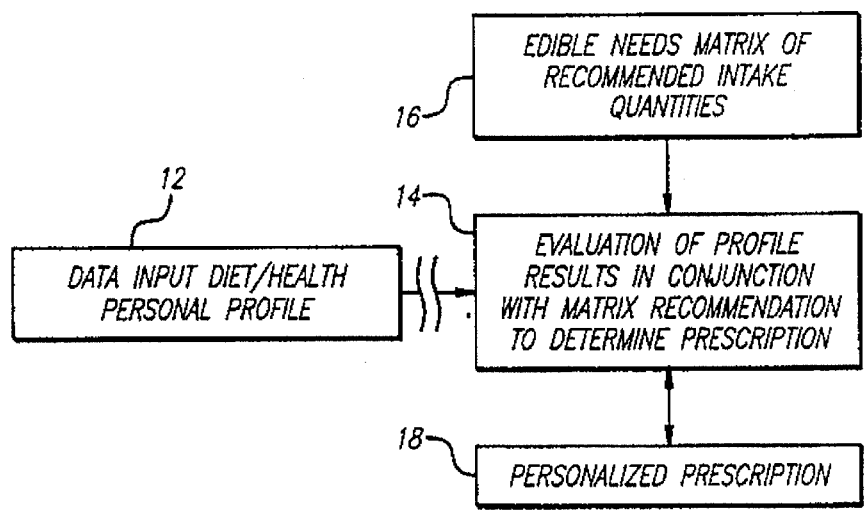
FIG. 1 is a high-level block diagram illustrating an exemplary operation of a system in accordance with the present invention.

Referring initially to FIG. 1, exemplary operational components of the system are illustrated. At the outset, a gamut of personal, physical, and health data is collected for the subject from a variety of sources (doctor's offices, laboratories, hospitals, wellness centers, etc., as well as, individual subjects themselves) as indicated by the data input block 12. For example, the information would include: sex, age, weight, type of work performed, along with a multitude of additional information on the habits, health and conditions of the individual including such parameters as blood pressure, blood picture (hematocrit, hemoglobin content, iron content, etc.), urine chemistry and so on.

The subject information (profile) may be accumulated as an initial step from several sources using various media, e.g., via forms filled by the individual or by the dietician/doctor; to determine an individual's health or dietary needs, as well as to serve the basis for follow up data. Additional pertinent information may be provided telephonically, or otherwise, for example, to include environmental data in the form of analyses of the water and air quality consumed by the individual, so as to indicate any nauseous substances to which the subject is exposed. Essentially, data may include any health related information supplied, on qualification, either on-line or off-line from the subject, the subject doctors' offices, laboratories, etc.

To consider an exemplary application, after the basic health and environmental information has been stored for a subjects's, edible-consumption information is supplied by the individual, typically on-line, at the time of consumption. Again, using the data input as represented by block 12, the individual's eating habits and drug intake are specified and stored.

Information from the data input block 12 in the form of a personal health profile is supplied to an evaluation block 14 that also receives pertinent data regarding human needs stored as indicated by an edible-needs block 16. The evaluation block 14 processes the personalized and generic data to arrive at recommended intake quantities (RIQ) for an individual subject. That is, the individual's requirements are defined preliminarily setting forth the various edibles including drugs, vitamins, antioxidants, minerals, proteins, fats, carbohydrates and so on for the specific individual.

The individual's edible intake is then compared with the recommended intake quantities (RIQs) and a list of deficiencies is generated as may be supplied to a personalized prescription block 18. For example, the personalized prescription block 18 may provide either a list for instructing the subjects or actual pharmaceutical edibles, as well as formulated nutritional substances for the subject. In either event, or by various partial arrangements, note that the edibles are individualized to meet needs and deficiencies of the individual. Thus, the individual receives a personalized prescription designed to address specific needs.

After an interval of use, the recommended intake quantities are reviewed, as by receiving further qualified information through the data input block 12 for comparative analysis and processing with regard to variations. Typically, after one or more reviews, a subject can be given a rather durable personalized prescription for attaining recommended intake quantities over an extended period, for example one year. Of course, periodic reviews at some level are desirable.

Figure 2:
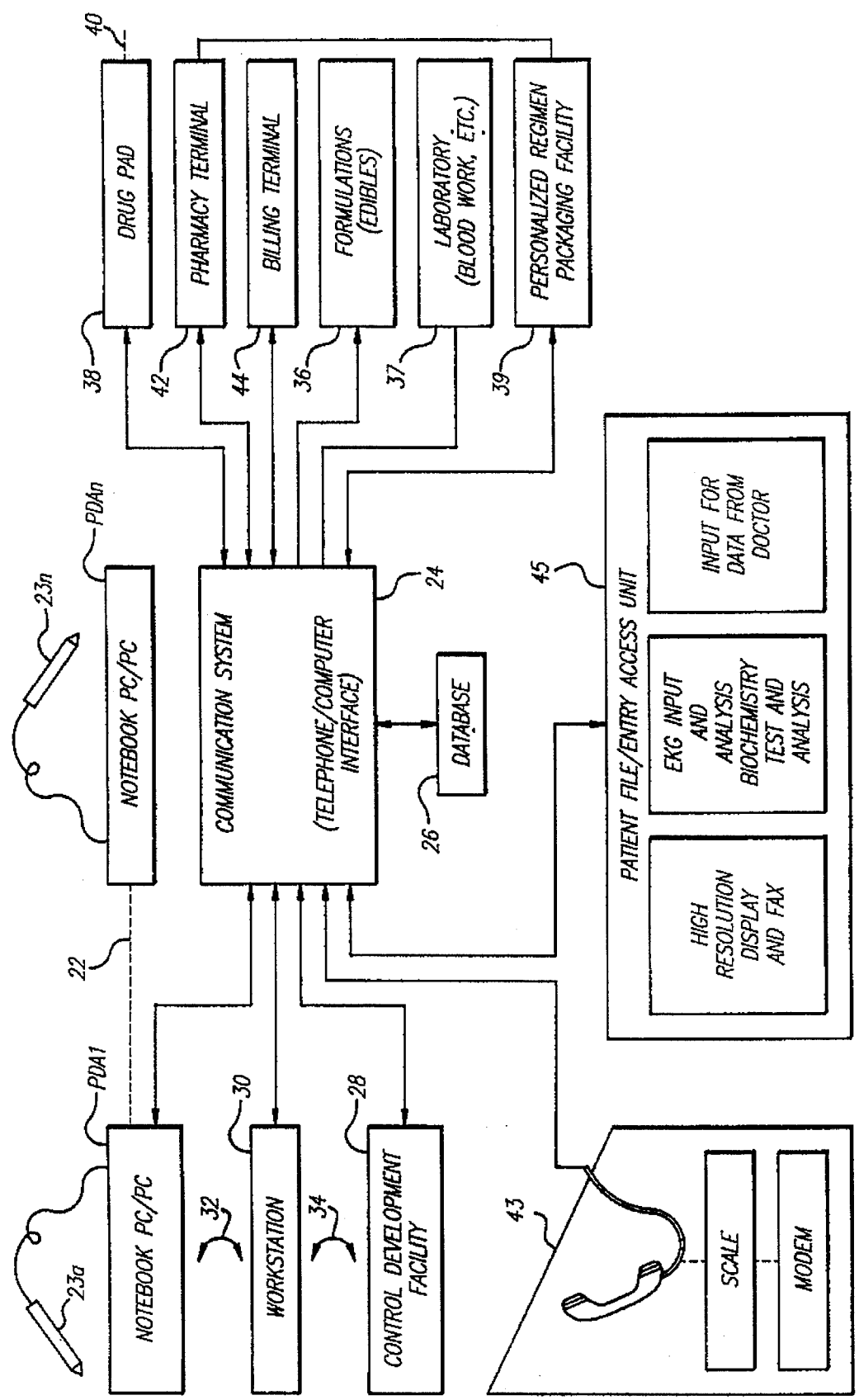
FIG. 2 is a structural block diagram illustrating specific components of the system in accordance with the present invention.

To further consider a structural embodiment of the system, references will now be made to FIG. 2 showing certain specific system components in greater detail. Generally, the components may be variously located to accommodate installation situations; however, for initial consideration, the system of FIG. 2 is presented without much concern for the physical locations of individual components. Still, typically, as explained below, major processing and storage operations will be located at a central station.

In FIG. 2, components are coupled by various communication capabilities, for example by telephonic/computer/facsimile capabilities. Signal data is communicated primarily by telephone. Notebooks or like computers PDA1-PDAn are provided to patients for use during the data acquisition intervals, typically, after an introductory session. As indicated by the dashed line 22, a plurality of notebooks PDA1-PDAn typically would be employed for the concurrent use by a multiplicity of individual subjects.

Structurally, the notebooks PDA1-PDAn may be similar and in that regard, the notebook PDA1 may take the exemplary form of a portable PC or automated notebook unit implemented for effective interface with a subject to accumulate data as explained in detail below. An attached portable bar-code reader 23a may be provided for the notebook PDA1, for example, sized and shaped like a pen. Other notebooks are similarly equipped, e.g., notebook PDAn with bar-code reader 23n. An individual may simply pass the bar-code reader 23 over the bar code on a package of a particular food item to record the pertinent information. Thus, the individual is only required to enter the meal code and the serving size. The system software correlates the product bar-code with the corresponding product nutritional data in the system.

Pursuing the notebook PDA1 as exemplary, it is connected through a communication system 24 to a database 26 (center) along with each of the other elements in the system. Note that elements are separately illustrated to simplify the explanation.

The communication system 24 may take the form of a public dial-up telephone network along with interface equipment including an audio response unit (ARU) and some computing capability for communication with all the other components as shown, including elements shown below the notebook PDA1, specifically, a control development facility 28 and at least one operator workstation 30. Typically, the interface portion of the communication system 24 along with the database 26, the control development facility 28 and the workstation 30 would be located at a central station of the system.

The database 26 (center) constitutes a substantial storage capacity along with organization logic for maintaining information in the form of health-related data, intake quantity data, recommended intake quantities for individuals, personal profile information, and established personalized prescriptions along with basic historical data on a multitude of individuals subjects.

In the disclosed embodiment, communications between the database 26, the facility 28, and the workstation 30 also may occur through the communication system 24 without entering a dial-up telephone facility. That is, internal communication enables direct accessing between these units. It is anticipated that most communications from the notebooks PDA1–PDAn will involve telephonic communication.

Generally, a subject utilizes the notebook PDA1 to store individual data that is periodically dumped through the communication system 24 to the database 26. With the accumulation of substantial data, the database 26 functions in cooperation with the control development facility 28 to process data and generate a preliminary matrix of recommended intake quantities for the subject. Note that during the course of such operation, an analyst's workstation 30 may be involved for clarification or for inputs relating to critical or unusual situations. For example, during the data accumulation phase, either a pattern of unusual data detected by the notebook logic, or a desire by the subject expressed by depressing a code key, will prompt communication directly between a notebook PDA1 and the workstation 30 as indicated by a loop 32. Note that a substantial number of workstations typically will be available to interface notebooks or the facility 28. Direct person-to-person communication accordingly may serve to advance the data accumulation or processing.

Recapitulating to some extent, during the development of a subject's profile and ultimately the subject's matrix of recommended intake quantities, communication may occur for computerized processing guidance as indicated by the loop 34. That is, intervals of interaction may be desirable between an analyst at the workstation 30 and the computer processing operations of the facility 28, depending upon individual conditions. Again a need for such may be indicated by the data in process.

With the completion of a preliminary personalized prescription, specifying recommended intake quantities, the control development facility 28, operating with the database 26 performs comparisons to determine individual needs for the subject. Processes treated in greater detail below, however, as a result, a personalized prescription is communicated to and generated for implementation by a formulations unit 36 and/or a drug pad 38.

The drug pad 38 and the formulations unit 36 may vary depending on the form of the prescription. In that regard, a form of personalized prescription facility 39 may implement the personalized prescription in the form of edibles as described in detail below.

Figure 7:
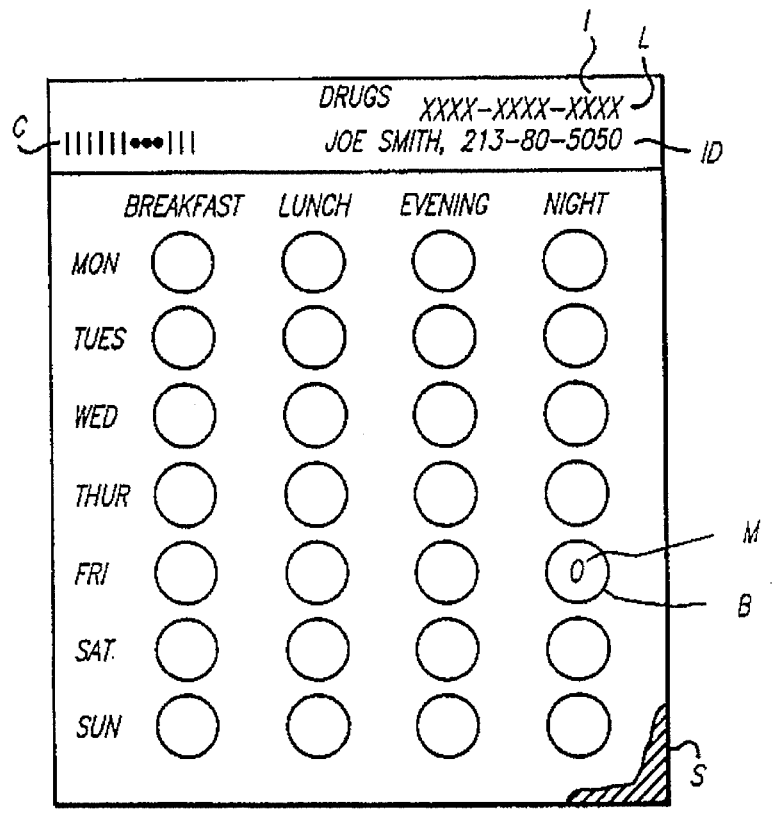
FIG. 7 is a diagrammatic representation of an exemplary drug regimen.
Figure 7A:
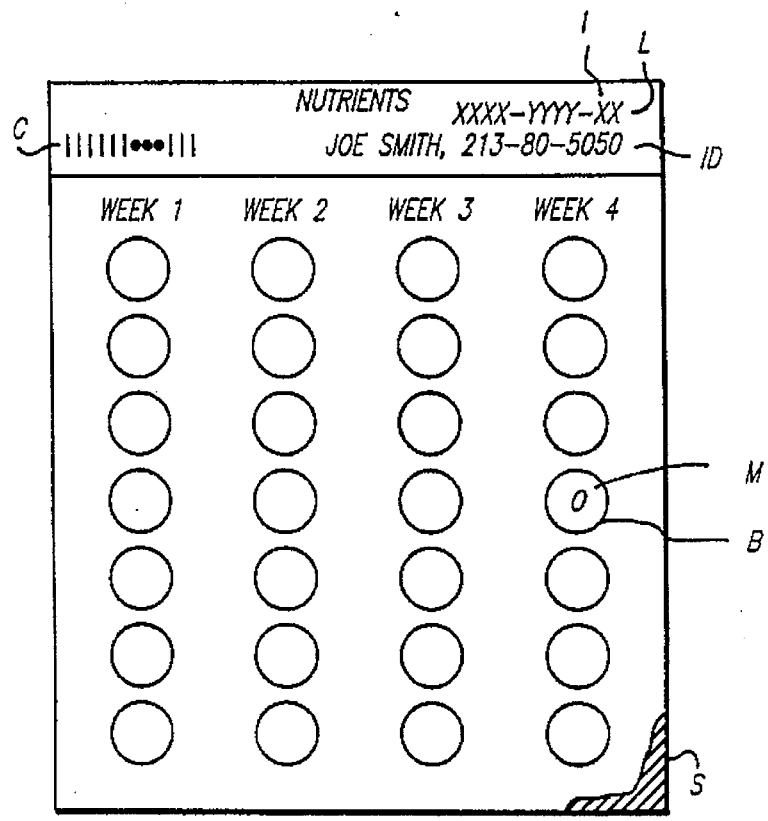
FIG. 7a is a diagrammatic representation of an exemplary nutrient regimen.

Edibles may take the form of a packaged drug regimen (see FIG. 7 and 7a) including an array of backed bubbles, for example, a 4×7 array labelled as shown in FIG. 7. Nutrient regimens (see FIG. 7a) recommended for relatively large groups of people may be prepackaged and special drug regimens may be custom packaged (see FIG. 7). Custom packaged drug regimens are particularly advantageous in geriatric care wherein elderly patients taking numerous drugs per day have a risk of drug mix-up. The regimen as illustrated comprises a backing sheet S of cardboard or the like, carrying container bubbles B for individual capsules M. Indicia on the sheet S includes a bar-code indicated at C (FIG. 7) including all pertinent data indicated at L (FIG. 7) along with a subjects identification ID and the ingredients I of the bubble contents. A personalized regimen packaging facility is indicated at 39 (FIG. 2) where such packaged drug regimens may be assembled, monitored or supervised by a pharmacist.

Further regulation or control of the formulations unit 36 may be effected by a drug pad 38 or other similar units as indicated by a dashed line 40. Other similar qualified control units include terminals at a doctor's office, a hospital, a wellness center, a dietician, or the like. Units such as unit 38 accommodate direct electronic communication from a subject's physician or other health professionals allowing the pharmacy terminal to provide the subject's physician with drug interaction analysis. Similarly, a laboratory indicated at 37 may download blood, urine, or like analysis reports to the central system to provide access to all subscribing entities.

A patient file access unit 45 (lower center) facilitates access by all healthcare providers. The patient file access unit 45 includes a high resolution display and facsimile means, as well as separate input and analysis units such as for EKG, biochemistry tests and so on.

For weight-loss applications, individuals may be provided with a scale and modem unit 43 with a telephone interconnected as illustrated, whereby periodically the individual may activate the scale and modem to automatically transfer to the central computer a measured weight. For such applications, the subject's progress will be compared to predetermined goals by the communication system 24. In the event the subject is meeting his or her weight reduction goals, nothing more is done. However, if the subject is not meeting his or her weight reduction goals, the central system may notify the program staff (analyst's workstation 30) who in turn may contact the subject to determine if the diet and exercise regimen recommended are being followed. Finally, a billing terminal 44 is provided in the system for accumulating and organizing billing information. Various criteria may be used for charges, as telephone time, computer time, analyst's time, case criticality and so on.

A pharmacy terminal 42 illustrates further flexibility in the gathering of data. Specifically, a perspective subject may use the terminal 42 (located in a pharmacy for example) to obtain preliminary information and perhaps initiate a relationship with a program of the system.

Figure 3:
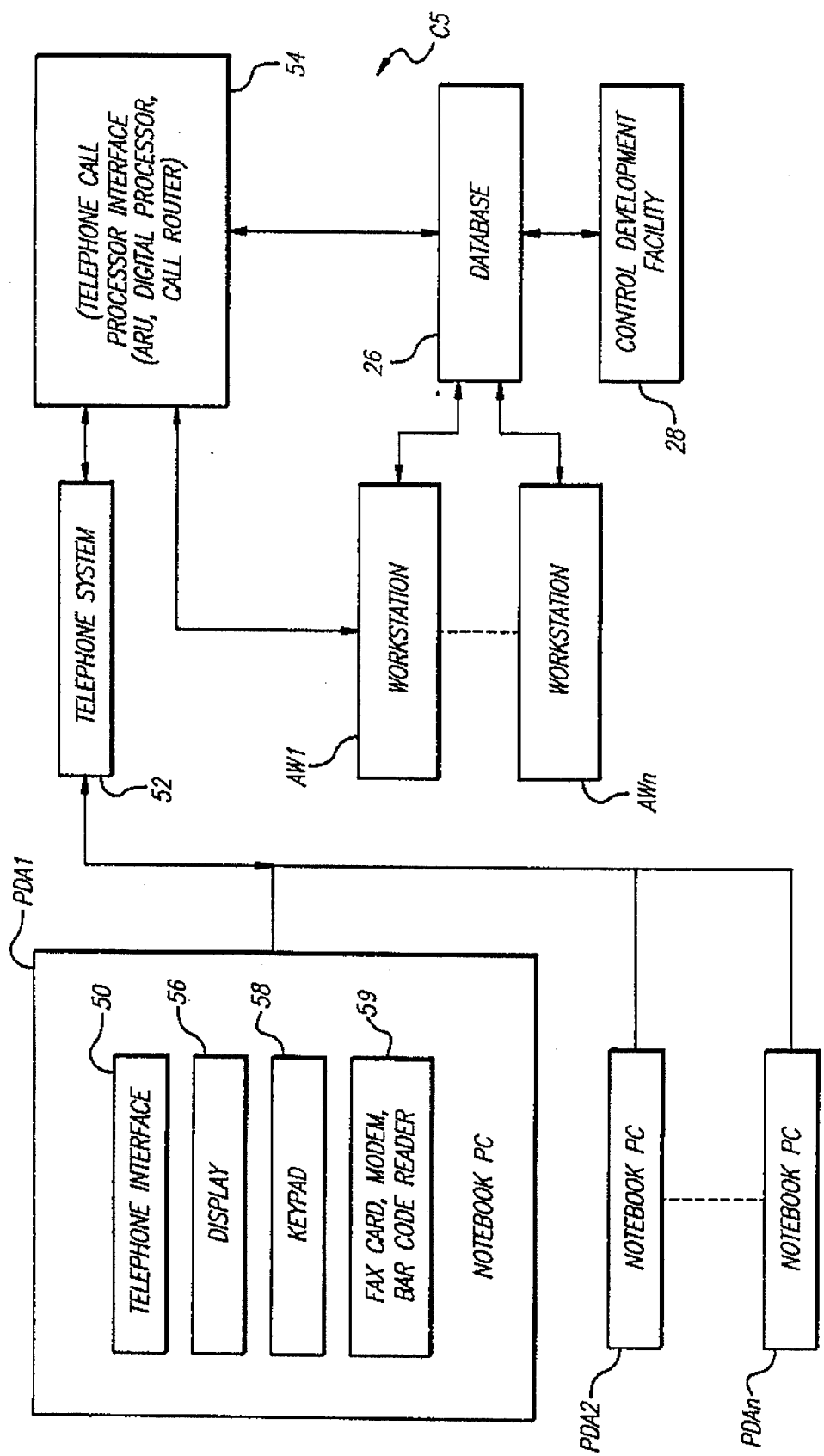
FIG. 3 is a block diagram showing a portion of the system of FIG. 2 in greater structural detail.

To pursue select aspects of the system at a more detailed level, reference now will be made to FIG. 3, illustrating a portion of the system of FIG. 2 primarily relating to the data acquisition phases and the generation of the personalized prescription.

As indicated above, the data acquisition phase includes two operations. Initially, in a typical case, either the subject, the subject's physician or other health person or entity inputs select items of detailed information to construct a file. Again, the detailed information may be input online or offline via forms, telephone interface, electronic mail, etc. Next, the subject's consumption of edibles is received from the subject and stored over a sampling period as a basis for generating an initial or proposed personalized prescription.

The data collection may be variously accomplished, as by the subject using a notebook PDA1. An exemplary form of the notebook PDA1 (FIG. 2) is illustrated in greater detail in FIG. 3 as a terminal (personal digital assistant) with a telephone interface 50, visual display 56, keypad 58, and collectively represented at 59, a fax card, a modem, a bar-code reader and so on. Note that in some instances of data accumulation, simply a telephone instrument may interface an audio response unit for data prompts and digital inputs.

In the system of FIG. 3, a plurality of terminals PDA1-PDAn are provided for use by individual subjects to supply input data. A detailed operating sequence is treated below; however, generally the terminals PDA1-PDAn are provided to subjects for specific periods (e.g. four weeks per year) to interface with the system so as to develop or refine the data in central storage.

Again, the terminals PDA1-PDAn may be similar and may take the form of a structure exemplified by terminal PDA1. In the embodiment as requested in FIG. 3, the telephone interface 50 operates through a telephone system 52 for communication with a central station CS including an interface 54. The telephone system 52 may take the form of a dial-up public network with the telephone interfaces 50 and 54 incorporating modems and other equipment to accomplish digital and audio communication. The interface 50 has the traditional telephone audio-digital capability. Audio cues are received to prompt touch tone digital responses.

Audio cueing, as well as digital processing is provided at the central station CS by the interface 54 which may incorporate an audio response unit (ARU), a digital processor and a call router. Such structures are well known in the prior art for cueing and receiving digital information and performing limited data processing.

The central station simply could be integrated in a comprehensive computer of considerable storage and processing capability, provided along with access workstations and other terminals. However, for purposes of simplified and direct explanation, separate components are illustrated in the figures and specifically treated below.

In the disclosed embodiment, the interface 54 serves a number of notebooks PDA1-PDAn, as well as a plurality of analysts' workstations AW1 through AWn. The interface is supported by a computer 26 cooperating with a facility 28. Overall, the workstations AW1 through AWn along with the interface 54 are controlled by the control computer and database 26 that also controls the control development facility 28.

Basically, the initial phase of the operation involves utilizing the telephonic interface (interfaces 50 and 54) to accomplish a comprehensive data cell in the interface 54 in the form of a subject's profile. As explained in greater detail below, the profile may be accomplished with or without the intervention of an operator located at one of the workstations AW1 through AWn.

After the completion of the subjects' health profile by the combined operation of the interface 54 and the computer 26, further processing is performed between the computer 26 and the control development facility 28 to accomplish a preliminary personalized prescription. During such operation, the terminal PDA1 and a workstation, e.g. AW1, may be interfaced if needed for supplemental data by person-to-person communication. As generally explained above and treated in further detail below, with the completion of the personalized prescription, a period of patient conformation is initiated followed by subsequent review. However, reference will now be made to FIG. 4 in further relationship to the generation, storage and processing of a subject's health profile data.

Figure 4:
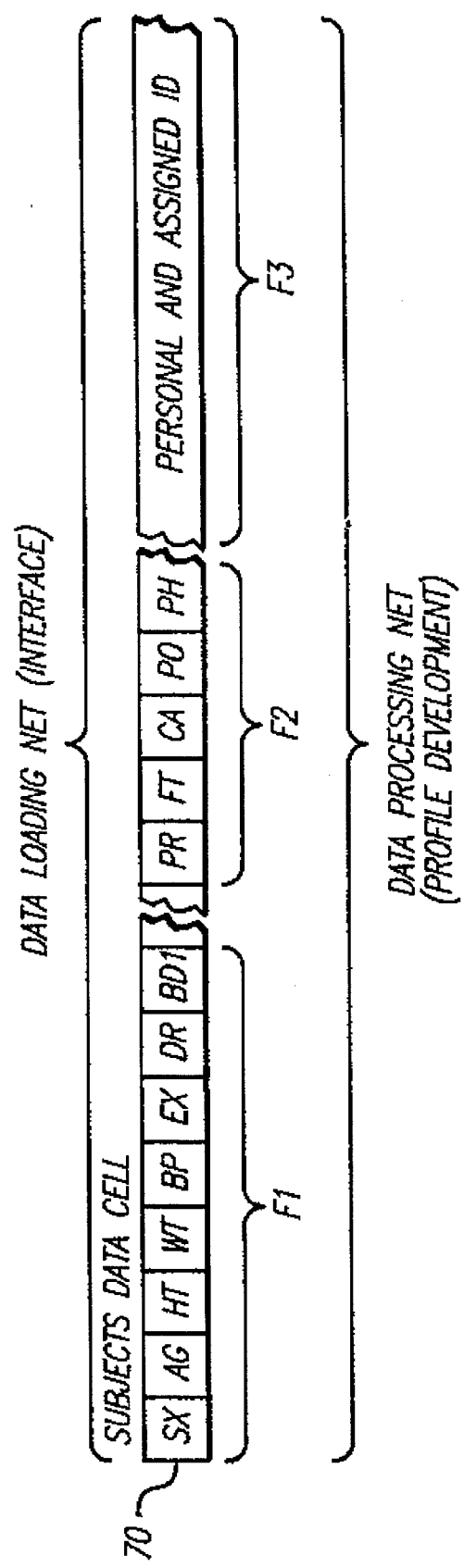
FIG. 4 is an exemplary subject's (individual) data cell.

With the admission of a subject to a program implemented by the system of the disclosed embodiment, a data cell or file is initiated in the computer 26 (FIG. 3) for storing detailed and comprehensive profile information on the subject. Typically, as explained above, the information is developed primarily through the telephonic interface as illustrated in FIG. 3. The subject (or his health care person) is given voice prompts and accordingly replies with keyed digital inputs, or in some instances vocally. Again, as indicated above, a data cell or file on a subject alternatively may be initiated or supplemented by the traditional use of forms. Information on the forms may be subsequently entered by a data entry operator or may be subsequently scanned in by a conventional scanner. Note also that a data cell or file on a subject may be created by the subject's physician, a wellness center or the like. In some cases, information on non-subscribing individuals may be randomly accumulated from healthcare facilities at no cost to the individual for future use. It will be appreciated that various techniques and procedures can be utilized in association with each of the terminals PDA1–PDAn (FIG. 3) to load the data cell 70 (FIG. 4). Specifically, the program may variously involve a medical doctor or other health professional. However, with preparation, the subject may provide certain health status information including age, weight, gender, and so on. Other data, as blood pressure, blood test results, urine test results and so on will of course involve a health professional as well as a testing laboratory. Consequently, inputs may be provided from different sources. However, for simplification assume that the subject collects the information and reduces it to a stored data format in the cell 70 utilizing one of the terminals PDA1 through PDAn.

FIG. 4 fragmentarily illustrates a subject's data cell 70 divided into a multiplicity of individual fields defining the subject's profile. Exemplary fields are designated in FIG. 4 indicating as follows:

| DESIGNATION | DATA |
| --- | --- |
| SX | SEX |
| AG | AGE |
| HT | HEIGHT |
| WT | WEIGHT |
| BP | BLOOD PRESSURE |
| EX | EXERCISE |
| DR | DRUG USE |
| BD1 | BLOOD CHARACTERISTIC 1 |
| PR | PROTEIN |
| FT | FAT |
| CA | CALCIUM |
| PO | POTASSIUM |
| PH | PHOSPHORUS |

As will be somewhat apparent, two forms of data fields are represented. The fields F1 represent the profile of the subject, that is physical characteristics and health-related conditions of the individual. The fields F2 represent data on edibles consumed by the subject. A field F3 carries a subjects data as personal characteristics and assigned representations, including a personal identification number (PIN).

Basically, by an analysis of the fields F1, a preliminary personalized prescription can be defined. By comparing the preliminary personalized prescription with the stored intake of the subject (as represented by the fields F2) supplements and modifications can be accomplished to provide a personalized prescription. Such processing operations are performed in combination by the computer 26 (FIG. 3) and the control development facility 28 as will now be considered in detail.

Consider an exemplary operating sequence utilizing the telephonic interface of FIG. 3 with audio or visual cues prompting the subject to enter data digitally element by element.

Sequence:

"Thank you for participating in the program. As you are aware, we are beginning the first of several brief exchanges to formulate and store your personal health profile. Typically these sessions will last about 15 minutes. First, please confirm your personal identification by entering your personal identification number now."

Subject enters personal identification number.

"Please touch '1' if you are female and '2' if you are a male"Subject enters sex.

"Please enter your age"Subject enters age.

"Please enter your height in inches"Subject enters height

"Please enter your weight in pounds"Subject enters weight.

"Our record now indicates that you are a lady, age 37, 5 foot 7 inches tall, weighing 115 pounds. If that is correct, please touch 1 before we proceed, otherwise touch 2"

And so the interface proceeds, prompting the subject to provide detailed information and thereby load the cell 70 (FIG. 4). During the course of a series of interface conferences (or otherwise as explained above), the cell 70 is loaded to contain the subject's comprehensive health profile. Indications are that most persons will be able to accomplish much of the loading without encountering any particular problems. Some detailed comments are deemed appropriate. The system accommodates transitions from a computer interface to a personal conversation. In that regard, the subject is instructed that personal contact can be established at any time by touching a particular code key or series of keys on the key pad 58. Also, personal contact will occur if the interface 24 in cooperation with the computer 26 (FIG. 3) detects any strange or weird data entries suggesting the need for person-to-person communication. In either event, the control computer 26 (FIG. 3) actuates one of the analyst's workstations AW1–AWn to place an analyst in communication with the subject involved allowing the flexibility of personal communication.

With the aid of person-to-person communication, unusual, confusing or complex situations can be clarified. Then operation can revert to the computer-interface operation of loading the subject's data cell 70. Consequently, during a series of sessions, the cell 70 is loaded, initially with the subject's health characteristic data (fields F1) and subsequently with the subject's edible intake (data fields F2) note that some data processing will normally be involved, particularly in the computer 26 in relation to the fields F2. The field F3 is completed and may involve a unique number generator or encryption techniques for identification data.

With the subject's health information complete, processing is initiated to develop the subject's profile within the facility 28. In that regard, the facility 28 incorporates logic as will now be considered with reference to FIG. 5.

Figure 5:
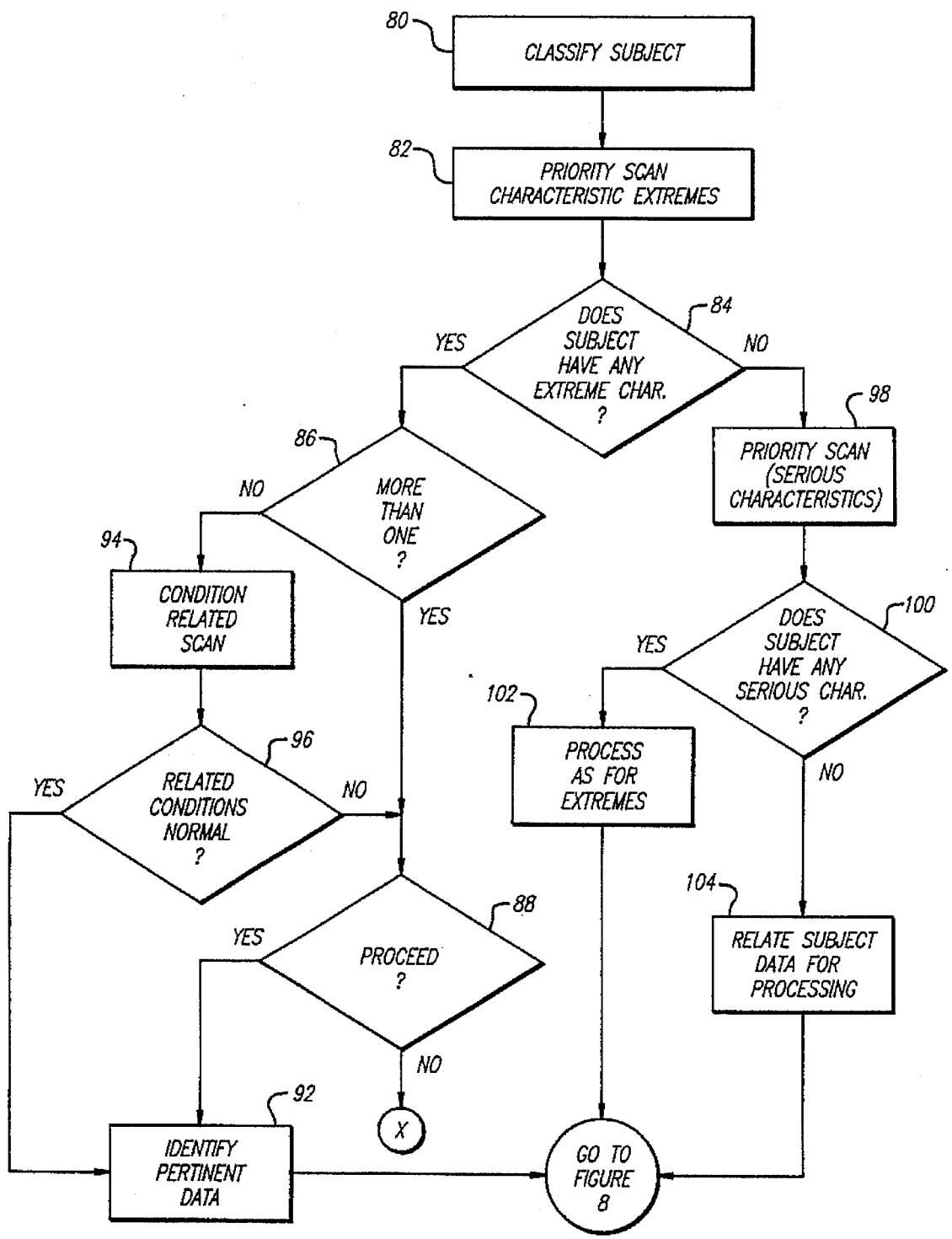
FIG. 5 is a logic flow diagram utilized in one application illustrating exemplary logic for a processing component in the system of FIG. 3.

At the outset, a subject is classified in a broad sense, for example, a female between the ages of "35" and "40". The classification step is represented in FIG. 5 by a block 80. The classification of a person is then pursued and tested with respect to various physical conditions or characteristics. For example, in a priority scan, each of the subject's characteristics or conditions is tested with reference to a range of normality. The scan serves to identify the existence of any extremes. The scan step is illustrated in FIG. 5 by the block 82.

As a result of the scan, any extreme conditions or characteristics of the subject are identified. For example, an extreme condition might be exemplified as diabetes, a very high level of cholesterol, or any of a number of other extreme health conditions for the subject's classification.

Typically, an extreme condition is defined as one that dominates the subject's health considerations. That is, an extreme condition typically commands dominant consideration with respect to the subject's personalized prescription of edibles.

After surveying a subject's data with respect to extreme characteristics, a logic determination is made as to whether or not any of the subjects' characteristics are extreme. The determination is indicated by the query block 84. If the subject has an extreme condition or characteristic, the process proceeds to a query block 86 for a determination of whether or not the subject has more than one extreme health characteristic. If the subject has a plurality of extreme conditions, the process advances to a query block 88 for a determination of whether or not the processing is to proceed.

In some instances, the existence of two extreme conditions withdraws the subject from further computer processing, indicating a need for direct individualized consideration by a health professional or analyst. If the conditions so indicate, the process advances from the query block 88 to a block 108 (FIG. 7, lower left), indicating the step of providing a printout on the subject for individual attention. Accordingly, a summary document is prepared for consideration by a health professional usually followed by a direct discussion with the subject.

Figure 8:
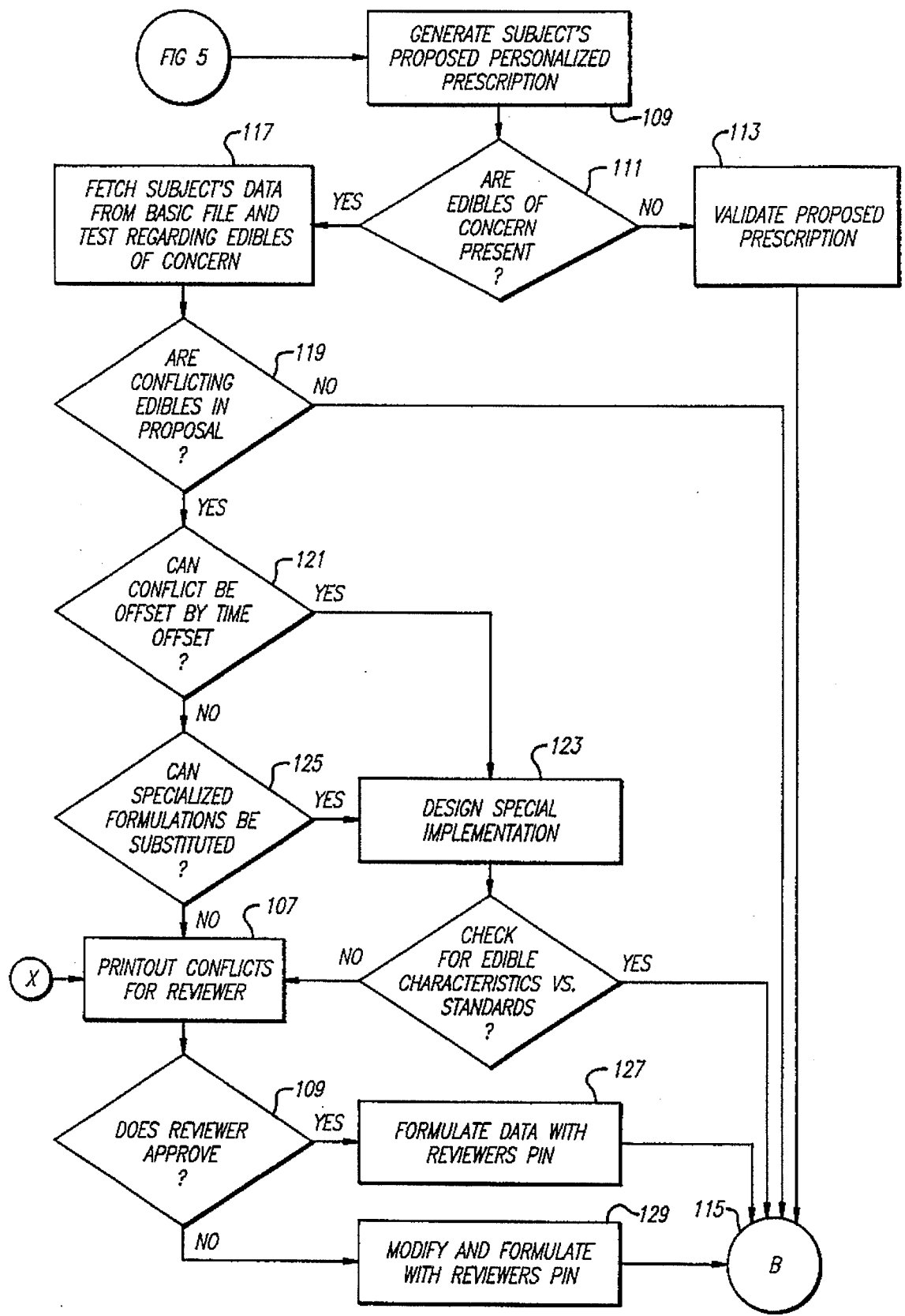
FIG. 8 is a first portion of a logic flow diagram illustrating exemplary logic for a processing component in the system of FIG. 2 embodied substantially in the control development facility.

In certain situations, it may be appropriate to do further processing on subjects with two critical conditions. For example, it may be desirable to scan other specific data for emphasis in relation to the conditions. Such processing is represented in FIG. 5 by block 92 and typically involves selectively fetching specific data that may be related to the critical conditions. With further processing in that regard, as indicated by the block 92, the system advances to the step of generating the proposed personal prescription (FIG. 8, block 109, upper center). As a result, the system processes data to accomplish the personalized prescription as treated below with reference to FIG. 8.

Returning to the query block 86 (FIG. 5, central left), if the subject has only one extreme health condition or characteristic, the process proceeds to a block 94 indicating a step of scanning for related conditions. For example, the presence of an extreme condition for a patient likely prompts concern with respect to several other data elements as stored for the subject. For example, indications of a critical heart condition may prompt a need for a host of data on activities, fat intake, tobacco use, etc. The step indicated by the block 94 involves a scan of such characteristics or conditions, followed by a step indicated by a query block 96.

Essentially, the question of the query block 91 determines whether or not further processing is desirable. For example, if the related conditions are somewhat normal, the process may advance to block 92 representing the step of flagging all pertinent data for use in developing the prescription (FIG. 8). Conversely, if the related conditions are not normal, a question arises as to whether or not further processing should be undertaken as indicated by the block 88. As explained above, depending on the decision of the query block 88, either the process advances to develop the prescription (FIG. 8, block 109) or a printout is provided for review (FIG. 8, block 107).

Returning to the block 84 (FIG. 5), if a subject has no extreme conditions or characteristics, a secondary priority scan is undertaken for characteristics that are serious, but not extreme. Again, any of a variety of characteristics might be classified as serious when they are outside particular ranges of normality. The scanning step is represented by a block 98. The next step, of query block 100, involves recognizing whether or not the subject has any serious characteristics. If the subject does have serious characteristics, the process may proceed to a block 102 providing logic substantially as described above with respect to extreme conditions or characteristics. That is, data is fetched, considered and tested to determine whether or not to proceed.

If a subject does not have any extreme or serious conditions or characteristics (block 100), the subject data is fetched to generate a preliminary personalized prescription as indicated by the block 109 (FIG. 8). That is, based on the subject's health characteristics or conditions, an idealized consumable format of edibles is prepared. The standard then is compared with an abstract of the edibles consumed by the subject (data fields F2, FIG. 4) to generate differentials. On the basis of that data, the subject is provided an initial personalized prescription indicating target consumption and possibly significant needs as well. Of course, as explained above the prescription may take many forms ranging from a list of supplements to a comprehensive schedule of edibles or packaged doses. The generation of the proposed personalized prescription as represented by the block 109 (FIG. 8, top center) essentially involves relating personal characteristics and conditions to established dietary and prescription specifications. Specifically, based on the subjects age, sex, weight and so on, certain basic nutrients or nutrients supplements have been established. Similarly, relationships are established between various drugs and human needs. Utilizing such standards, the system generates a proposed personal prescription of edibles for the individual subject. Such a preliminary compilation is then processed utilizing a format of the disclosed embodiment. Specifically, reference will now be made to FIG. 8 to consider the exemplary process.

The generated proposed personalized prescription for a subject (block 109) is tested for presence of edibles of concern (block 111). Essentially, some proposed personalized prescriptions may involve solely bland edibles deemed to be completely safe for human consumption under virtually any considerations. If such is the case, and no edibles of concern are present, the query of block 111 advances the process to validate the proposed prescription as indicated by block 113 advancing the process to the circle 115 designating a continuance in FIG. 8a.

Returning to the query block of 111 a determination that edibles of concern are present advances the process to a block 117 as a first step in relating the edibles to the subject's profile. After fetching the subject's data from the basic files, a query step involves the test for conflicting edibles in the proposed prescription (block 119). The test is basically whether or not the subject has total tolerance for any edibles of concern identified in the proposed personalized prescription. If not, the process proceeds advancing to the circle 115. However, if the identified edibles of concern present a conflict, the process proceeds to another query step as represented by the block 121.

In certain instances, a dietary conflict can be off set, as for example by time displaced doses. The query block 121 raises such a possibility. If off set can be employed to resolve the conflict, the process proceeds from the query block 121 to a step represented by block 123. Essentially, the operation of block 123 involves designing time into the implementation of a proposed personalized prescription to accomplish the resolution of a conflict. As a specific example, a subject may tolerate a particular edible if dosages are spaced apart by several days.

Returning to the query block 121, if the conflict can not be off set by time displacements, the process proceeds to a query block 125, i.e., "Can specialized formulations be substituted?". References to the possibility that some form of the conflicting edible maybe suitable for the subject. If so, the process again proceeds to the step of block 123 involving the design of a special implementation for the prescription.

If specialized formulations are not available, resulting in a negative path from the block 125, the system proceeds to a printout stage as indicated by the block 107. Essentially, after having exhausted various possibilities for solution the system prints out the data (prescription and considerations) for consideration by a reviewer. Essentially, human intelligence is now called upon to consider the situation and exercise possible intuitive judgement. If the reviewer approves the proposed prescription as formulated, such action is indicated and confirmed by the entry of the viewer's personal identification number (PIN). The step as indicated by the block 127 resulting in the data being advanced to the circle 115.

As an alternative, the reviewer may modulate or totally reformulate the proposed personalized prescription in a step as indicated by the block 129. Such a prescription is then advanced, again with the reviewer's personal identification number (PIN) for tracking and responsibility purposes.

Figure 8A:
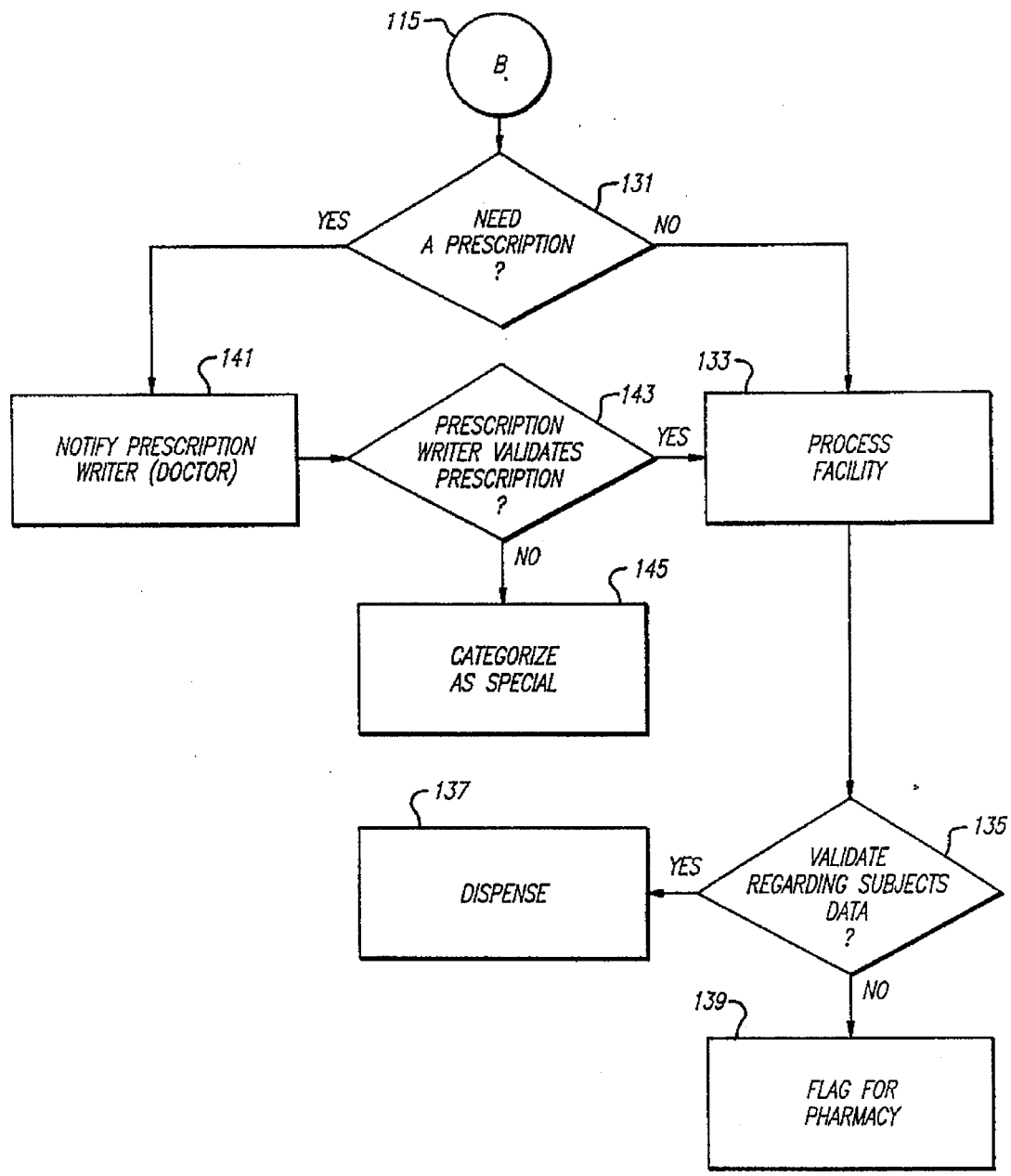
FIG. 8a is a second portion of the continued logic flow diagram of FIG. 8.

As the process attains the circle 115 (B) it is advanced to the diagram of FIG. 8a at the similarly designated circle 115 (B). The next step involves a query of whether or not the personalized prescription requires a prescription approval. That is, depending upon the local processing, various ingredients or edibles will require approval by a medical practitioner as in the form of a medical prescription. For example, the proposed personalized prescription may require the approval or validation of a medical practitioner, e.g., doctor, dentist or so on, prior to issuance. If no medical prescription is required, the process proceeds to a step represented by a block 133 indicating the implementation of the prescription. Subsequent of implementation, the prescription is tested or validated as indicated by the query block 135 with respect to the subject's profile or data. If the formulation totally conforms and is validated, it is dispensed as indicated by the block 137; however, if validation does not occur, the prescription is flagged as indicated by a block 139, for consideration by a pharmacist or other medical expert.

Returning to the query block 131, for edibles requiring a medical prescription, the process advances to a step represented by a block 141 introducing a prescription writer for purposes of approving the prescription. The operation may simply involve a computer interface or various other communication techniques may be involved.

If the prescription writer does not approve the prescription as a medical prescription, see query block 143, special action is required as indicated by the block 145. Specifically, the prescription writer presumably will act on the matter to accomplish a resolution.

If the prescription writer validates the prescription (block 143) the process again advances to block 133 indicating that the prescription is to be implemented as described above. Accordingly, a personalized prescription is accomplished for a subject.

To further explain the system of the present invention, consider another exemplary procedure in some detail. Of course, the system is susceptible to a multitude of variations and implementation techniques. Accordingly, the following is a simplified example involving other aspects of the process.

Assume the subject is a male, age 40 and has been referred to a nutritionist by his doctor. In accordance with a program as implemented, the subject might be shown a video presentation to explain the overall program. Next, the subject could be instructed in the use of a terminal PDA1 and its operation to provide system data as explained in detail above. Typically, the subjects would then proceed during a data acquisition period, after which a subsequent visit would be scheduled.

During the data acquisition period, specifically during several operating intervals, the subject would load the data cell 70 (FIG. 4) using the terminal PDA1. In that regard, the subject may be given specific telephone times for data dumps, or the subject may simply be at liberty to enter and transfer information at his convenience.

In due course, assuming the completion of health data in the storage cell 70, further assume generation of a preliminary profile of the personal data to indicate as follows for the subject:

| CHARACTERISTIC | VALUE |
| --- | --- |
| SEX | MALE |
| AGE | 40 |
| WEIGHT | 200 |
| HEIGHT | 5'10" |
| ACTIVITY LEVEL | SEDENTARY TO MODERATE |
| SMOKER | YES, 1 PACK/DAY |
| CHOLESTEROL LEVEL | 250 (HIGH) |
| EXPOSURE TO SUN | MODERATE |
| INTAKE OF SALT | MODERATE TO HEAVY |
| INTAKE OF EGGS | HEAVY |
| CURRENT MEDICATION | NONE |
| KNOWN DEFICIENCIES | NONE |

A high cholesterol level prompts concern within the compiler logic regarding related conditions, e.g. weight, activity, use of cigarettes, foods, etc.

As indicated, the subject is significantly overweight and gets little exercise. As a smoker (with a high cholesterol level) he is at risk for cardiovascular problems. The printout is provided for analysis by a health professional and a consultation occurs.

To enhance the example, assume that the subject indicates an unwillingness to significantly alter his diet, however, he does agree to cut down on his intake of eggs, which appear to be the greatest contributor to his elevated cholesterol levels. Following an interval of data collection, e.g. a month, during which data is accumulated, reports are prepared for follow up visits, at which time the subject will receive further dietary advice and a personalized prescription.

To pursue the example, the reports might include the man's average daily intake of nutrients as compared to recommended quantities. Further varied intakes may be suggested including antioxidants and chromium. Specifically, beta carotene, vitamin E and selenium might be recommended to provide the prophylactic effects of the antioxidants. An increased dosage of vitamin C also might be recommended in view of the fact that the man is a smoker. For example, recommended additional quantities of 200 mg. of vitamin C is considered effective for each pack of cigarettes smoked by a subject. Typically the computer and data base will raise such questions to assist his healthcare expert.

Of course, numerous other specifics may be embodied in the subject's personal prescription. Thus, the system may be implemented to provide the subject with information to effectively alter his diet and thereby accomplish a significant health improvement.

After placing a patient on a particular regimen, periodic monitoring might result in further modifications or enhancements. For example, a patient might be effectively served by the utilization of a terminal PDA1–PDAn for a period of a few weeks each year. During that time, refinements to dietary or medication requirements may be made in the personalized prescription.

As an alternative or supplement to the operation of providing a subject information, the system may actually generate pills, food packets (for example, see FIG. 7), or even a complete menu for consumption by a subject. Specifically, the pharmacy terminal 42 (FIG. 2) may simply formulate appropriate doses of individually defined edibles formulated for the specific subject. Basically, the computer system 24 simply controls custom formulation by the pharmacy terminal 42.

One example of the custom formulation by the pharmacy terminal 42 is illustrated by the following example relating to geriatric care. An elderly patient taking six drugs per day may be inclined to mix-up his or her drug intake. Accordingly, a organized drug regimen is provided by the personalized regimen packaging facility 39 in the form of pill packages, as illustrated in FIG. 7. Typically, specific medications may reduce ion levels in the patient's body, thus, increasing the level of toxicity of some of the other medications prescribed for the patient. In such cases, the patient may be required to increase his or her intake of nutrient supplements to compensate for certain ion losses in the body. For example, assume the following prescription for an individual:

| Medication | Time of Day | Reason for Prescription |
| --- | --- | --- |
| Digoxin | Breakfast | Atriah Abrillation: Problem. Medication for lowering the heart rate, raising the strength of the left ventricle contraction |
| Firosinide | Breakfast | Diuretic. |
| Enalapril | Breakfast/Supper | Angiotinsen converting enzyme inhibitor to treat heart failure and hypertension. |
| Warfarin | Supper | Anti coagulant to decrease risk of embolic events (strokes, clots). |
| ABA | At 3 meals | Non steroid anti-inflammatory |
| Nortiplylline | Noon | Anti-depressant. |

The computer system 24 performs an interaction analyses and finds that furosionede lowers sodium (No) and potassium (K) levels in the body. Moreover, the computer system 24 uncovers that in the event a patient on Digoxin shows the blood serum level to be low in potassium, susceptibility to Digoxin toxicity is increased. The symptom for Digoxin toxicity is mild kidney failure. Thus, in such a scenario, the patient would be advised to take potassium as a dietary supplement to offset the potassium losses. Potassium may be included as part of the patient's daily medication and/or the patient's nutritional pill regimen.

The personalized regimen packaging facility would provide the patient with packaged regimens as illustrated in FIG. 7. To order the particular drug regimen for a particular patient, the physician may simply enter the drug type, dosages and the times of drug intake into the drug pad 38. After entering the information, the physician may sign the prescription. The patient may order the prescription by presenting a credit card or the like to the billing terminal 44. The prescription information is then transmitted to the Personalized Regimen packaging facility, where an order number is assigned. The original prescription may be transmitted directly to the Personalized Regimen Packaging. Entering the patient name and order numbers triggers the automated personalized regimen packaging process. Once the regimens are packaged, they may be directly transmitted to the patient, pharmacy or any intermediate location from where they are to be dispensed to the patient.

The system of the present invention processes personal patient files in conjunction with new laboratory analyses, e.g., blood chemistry or urinal analysis to assess potential high health risk situations. Readily available information accumulated from general sources, as well as updates on new laboratory information are used by the system to automatically detect critical conditions. To that end, the system incorporates logic as will now be considered with reference to FIG. 6. At the outset, when communication with the central system is initiated for purposes of seeking information or providing updates, for example from a laboratory, the calling entity's identity is verified (PIN) to determine if the calling entity is allowed access to the system. This step is illustrated by the block 108.

In the event the caller is denied entry, as on the basis of inadequate or improper identification, a record may be implemented for possibly meaningful information. Specifically, as indicated by a block 110, the caller is requested to provide information in accordance with the intentions of the call. Basically, a record may be formed and to the extent practical, the data is correlated to the file as indicated by the block 112. Thereafter, the process advances to the block 114 and communication is terminated.

Alternatively, in the event the caller is allowed access on the basis of the test, the process advances to the block 116, wherein identification information on the particular subject is sought. For example, assume that the XYZ laboratory is seeking access to the system to update a particular subject's profile (XXXX) with recent laboratory analysis on the subject's blood. Accordingly, a pin number (XXXX), a social security number or other data identifying the subject must be entered as a condition to proceeding. With the entry of such identification data, the process advances to the block 118 indicating the step of loading the laboratory analysis into the subject's data cell 70. Accordingly, the profile of the subject is updated to reflect current information, with the updating of a particular subject's data cell (block 118), the process is triggered to review the subject's modified data in view of the modifications. Specifically, as indicated by the block 120, a step is initiated as for early detection. That is, data is fetched to execute a comparison of conditions.

Figure 6:
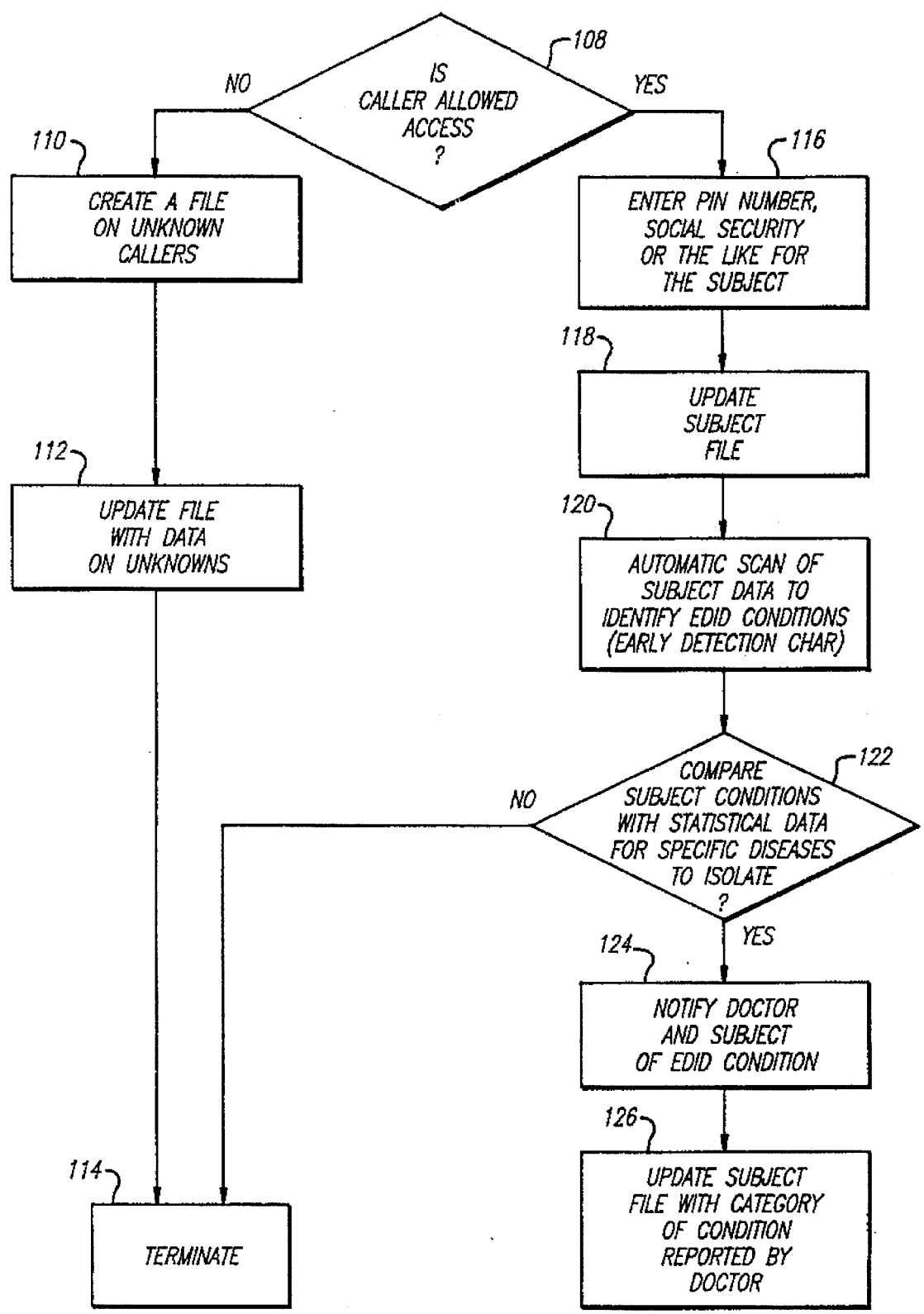
FIG. 6 is a logic flow diagram illustrating exemplary logic for a processing component in the system of FIG. 2 in a specific application to facilitate early detection of diseases.

As represented by the query block 122, a subject's conditions are analyzed to determine an indication of possible specific diseases. If no such indication is manifest, the process proceeds to the termination block 114 with the subject's record updated and preserved. Alternatively, if the comparison of block 122 indicates the likely presence of a disease, the system advances to a block 124 indicating communication of the facts to the subject's doctor or other health practitioner. With new consideration, the doctor receiving the report likely will indicate the results of his analysis in the subject's file. This step is illustrated in FIG. 6 by the block 106.

To consider another exemplary case, a high blood pressure patient completes a nutritional counselling session which results in the patient receiving amongst other recommendations, a recommendation that the patient balance the potassium (PO) intake in his/her diet with the sodium (NO) intake. It has been observed in certain epidemiological tests that in certain cases where patients are taking hypertension retarding drugs that up to 30% of those patients can cease using hypertension drugs and on the average the remaining patients could reduce the use of hypertension drugs by about 50% simply by balancing the sodium and potassium intake. In the current invention it is envisioned that after the patient/subscriber has adjusted his/her diet either through food intake or dietary supplements that the patient would measure his/her blood pressure at designated time intervals. The patient would do this measurement through a blood pressure meter connected to his or her Notebook PC. The use of the Notebook PC allows for simplified and more accurate measurement of blood pressure and allows for no work recording and subsequent processing.

After measuring the person's blood pressure based on information determined from the patient and his physician, the Notebook PC depending on the blood pressure test will advise the patient/subscriber to take a particular hypertension pill on a given day or recommend that the patient not take any drugs that day. Summary of the blood pressure and medication history of the patient will be available for review by the physician and the patient at the time of their normally scheduled meeting.

It is also noteworthy that the billing terminal 44 (FIG. 2) maintains a record of the activity with specific subjects to afford effective billing. Generally, various techniques involving time, personalized consultations as well as other considerations may be recorded within the billing terminal 44 for the preparation of subject statements.

Figure 9:
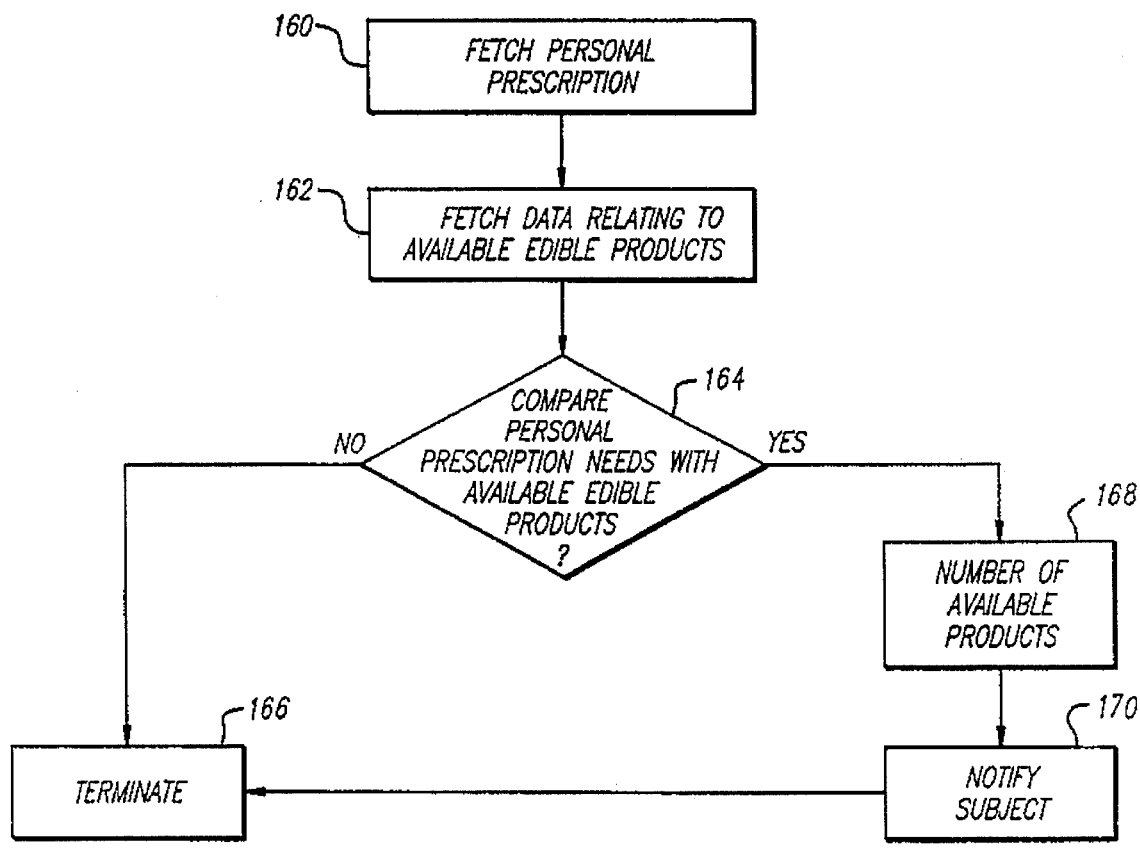
FIG. 9 is another logic flow diagram of processing as may be embodied in the system of FIG. 2.

The system of the present invention may be effectively employed to refine edible consumption for persons in such a manner as to serve basic desires and health needs. For example, a person may simply refuse to reduce a quantity of fat consumed. However, by selective food choices the health of such person can be significantly improved. Accordingly, the system hereof can be utilized to provide guidance for individuals, affording healthy choices. Typically, some compromise is involved; however, a person's general health and well being may be substantially improved by accommodating dietary desires with prudent alternatives. As indicated above, the system of the present invention accumulates substantial data on individual subjects regarding actual and idealized food intake. The system also accumulates vast quantities of information on edibles, their content, form, and so on. Essentially, in accordance herewith, such data offers the possibility of considerably improving a subject's health on the basis of diet, without disregarding the subject's individual tastes. The process is illustrated in FIG. 9 and will now be considered.

As indicated by block 160, data is fetched from storage on an individual subject relating to dietary needs and limitations. Somewhat concurrently, as indicated by a block 162, data is fetched from storage on related edible products. For example, the edible product information might reveal a multitude of different hot dogs, each involving specific formulations and ingredients.

With the data at hand, comparisons are executed seeking edible products that most effectively serve the subject's needs and desires. Pursuing the example, based on a recorded desire of the subject to consume hot dogs, a scan of available hot dogs may be undertaken seeking characteristics most desirable and accommodating to the subject's dietary needs. The processing operation is indicated in FIG. 9 by a query box 164 searching for select edibles. If a test produces no "hits" the cycle is terminated as indicated by the block 166, presumably to initiate another cycle of operation. Such would be the case if no available form of hot dog would be acceptable for consumption by the subject.

Returning to the query block 164, a more likely possibility would involve the location of certain edibles satisfactory for the subject. With regard to each of the "hits", acceptable edibles are tallied (block 168) and may be limited. For example, it may prudent to limit the number of "hits" to a specific number of the best edibles. Perhaps, three forms of hot dogs would be a sufficient number to list. Accordingly, moving from the block 168 to a block 170, the formulated list is prepared for transmission to the subject and the cycle is repeated to another edible category. Ultimately, after several cycles, a list of edibles is generated that would be most satisfactory for the subject's health. The list may be provided to the subject directed for guidance or alternatively, the list may serve as a basis for a specific menu for the subject.

Of course, various other processing operations can be utilized with respect to the gross volume of data on edibles and subjects. Also, dietary guidance for subject's can be periodically refined in the interests of appetite, health, available edibles and dietary knowledge.

What is claimed is:

1. A health care system for specifying a personalized and comprehensive prescription of edibles to individual subjects, comprising:

an edible-needs storage means containing health and edible generic needs data relating to said individual subjects, and adapted to receive conditions and characteristics data for said individual subjects;

a plurality of input terminals coupled to said edible-needs storage means for providing said conditions and characteristics data for said individual subjects;

a health computer coupled to any one or more of said plurality of input terminals to receive said conditions and characteristics data for said individual subjects and to identify for each of said individual subjects data indicative of extreme conditions or serious characteristics, said health computer prioritizing said data indicative of extreme conditions or serious characteristics for correlation with said health and edible generic needs data stored in said edible-needs storage means for each of said individual subjects to provide a personalized and comprehensive prescription of edibles.

2. A health care system according to claim 1, wherein said input terminals include telephonic devices for coupling to said edible-needs storage means.

3. A health care system according to claim 2, further including a telephonic interface for prompting said telephonic devices.

4. A health care system according to claim 1, wherein said edible-needs storage means further includes:

first subject data cells for storing personal data representative of an individual subject's weight, age and extreme or serious conditions;

second subject data cells for storing consumption data representative of said individual subject's record of consumed edibles; and third subject data cells for storing identification data representative of said individual subject's identification.

5. A health care system according to claim 1, wherein said health computer scans the conditions and characteristics data of said individual subjects to prioritize data representative of said individual subjects' extreme conditions or serious characteristics.

6. A health care system according to claim 5, wherein said health care computer limits access to said first subject data cells on the basis of said identification data stored in said third subject data cells.

7. A health care process for developing a personalized and comprehensive specification of edibles for an individual subject, comprising the steps of:

storing comprehensive treatment data on relationship of health to edibles;

receiving and storing individual data from a plurality of sources on an individual subject relating to characteristics and conditions of said individual subject;

scanning said data on said characteristics and conditions of said individual subject to identify any extreme or serious characteristics; and correlating said characteristics and conditions of said individual subject with emphasis on identified extreme or serious characteristics to specify a schedule of edibles in accordance with said comprehensive treatment data.

8. A health care process according to claim 7, further including a step of classifying individual subjects in relation to said comprehensive treatment data.

9. A health care process according to claim 7, further including a step of telephonically interfacing said individual subject to receive said individual data for storing.

10. A health care process according to claim 7, further including a step of imposing controlled access by said individual subject to store said individual data.

* * * * *